United States Patent [19]

Fukasawa et al.

[11] 4,289,706
[45] Sep. 15, 1981

[54] METHOD FOR PRODUCING 1-NITROANTHRAQUINONE

[75] Inventors: Akira Fukasawa, Toyonaka; Shinzaburo Masaki, Takarazuka; Norio Serizawa, Ibaraki, all of Japan

[73] Assignee: Sumitomo Chemical Company, Limited, Osaka, Japan

[21] Appl. No.: 61,382

[22] Filed: Jul. 27, 1979

Related U.S. Application Data

[63] Continuation of Ser. No. 853,753, Nov. 21, 1977, abandoned.

[30] Foreign Application Priority Data

Jan. 6, 1977 [JP] Japan .................................... 52-695

[51] Int. Cl.$^3$ ............................................. C07C 50/18
[52] U.S. Cl. .................................................. 260/369
[58] Field of Search ................................ 260/369, 688

[56] References Cited

U.S. PATENT DOCUMENTS

| | | | |
|---|---|---|---|
| 1,856,231 | 5/1932 | Stowell | 260/369 |
| 3,766,222 | 10/1973 | Hartwig et al. | 260/369 |
| 3,925,426 | 12/1975 | Vogel | 260/369 |
| 3,968,130 | 7/1976 | Szekely | 260/369 |

Primary Examiner—Patrick Garvin
Assistant Examiner—Raymond K. Covington
Attorney, Agent, or Firm—Stevens, Davis, Miller & Mosher

[57] ABSTRACT

Anthraquinone is nitrated using a mixed acid comprising sulfuric acid and nitric acid, the concentration of sulfuric acid being 70 to 76% by weight and the amount of nitric acid being 33 to 55% by weight based on the total weight of sulfuric acid and nitric acid, whereby 1-nitroanthraquinone is obtained in a high yield and a high purity.

6 Claims, 1 Drawing Figure

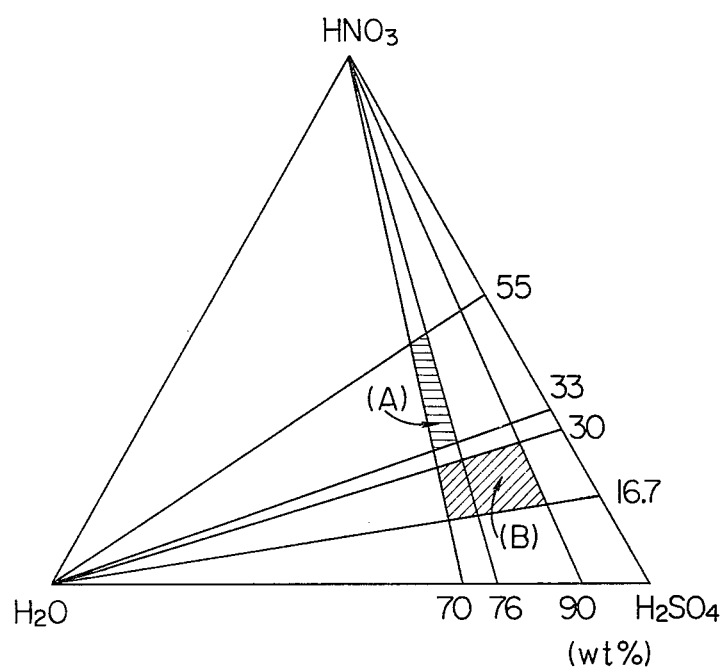

METHOD FOR PRODUCING 1-NITROANTHRAQUINONE

This is a continuation of application Ser. No. 853,753, filed Nov. 21, 1977, now abandoned.

The present invention relates to a method for producing 1-nitroanthraquinone using a mixed acid.

It is well known that 1-nitroanthraquinone is obtained by nitrating anthraquinone with nitric acid or a nitrate in sulfuric acid or with an excess of concentrated nitric acid. When the nitration is carried out under known conditions, however, dinitroanthraquinones are always produced as by-products by further nitration of the produced 1-nitroanthraquinone before all the anthraquinone in the reaction system are converted to 1-nitroanthraquinone. In addition, the α-nitration is inevitably accompanied with β-nitration. In the conventional manner, therefore, the reaction product containing at best about 65% by weight of 1-nitroanthraquinone is obtained and moreover it contains 20 to 30% by weight of dinitroanthraquinones difficulty separable.

For the reasons described above, there have been made many attempts to control the formation of dinitroanthraquinones to obtain 1-nitroanthraquinone in a higher yield. For example, there have been proposed an improved process in which the nitration is carried out in sulfuric acid (U.S. Pat. No. 3,766,222), a process in which the nitration is carried out in phosphoric acid (U.S. Pat. No. 3,786,073), an improved process in which the nitration is carried out in nitric acid (U.S. Pat. No. 3,798,243 and U.S. Pat. No. 3,836,601), and a process in which the nitration is carried out in an inert organic solvent (U.S. Pat. No. 3,925,426).

Further, prior art references are as follows:
1. R. Oda and K. Tamura, Bull. Inst. Phys. Chem. Research (Tokyo), 16, 950 (1937)
2. The Chemical Age (Dyestuffs Monthly Supplement) pages 29 and 30, Oct. 8, 1927
3. U.S. Pat. No. 2,302,729

But these processes have some drawbacks in production on a commercial scale.

According to the description in U.S. Pat. No. 3,766,222, it is preferable to allow the nitration to proceed in a heterogeneous system comprising a 70 to 90% sulfuric acid at a temperature of about 20° C. to about 60° C., until the yield of 1-nitroanthraquinone reaches about 75% by weight. According to a detailed investigation of this process by the present inventors, it is very difficult to obtain 1-nitroanthraquinone in a yield of 75% by weight even though the nitration is carried out under the conditions described above, and in most cases the yield is only about 65% which is about the same as the yields of the well-known methods. Only when the nitration is carried out according to one example given in said U.S. patent, does the yield of 1-nitroanthraquinone reach 75% by weight after a nitration time of about 12 hours. In this process, however, when the crude 1-nitroanthraquinone is separated from the resulting nitration mixture by discharging the mixture into a large amount of ice water followed by filtration, a large amount of waste mixed acid is produced as a filtrate. More concretely speaking, the amount of a 78% sulfuric acid is 8 parts by weight per part by weight of anthraquinone, and moreover nitric acid is used in such a large excess as 2.4 parts by weight over 0.36 part by weight to be consumed in the reaction. Consequently, on discharging the nitration mixture into ice water, such large amounts of sulfuric acid and nitric acid become diluted with a large amount of water to make a large amount of a waste mixed acid. From the industrial point of view, it is not only undesirable in terms of environmental protection but also very uneconomical to neutralize and discard such a large amount of the acid. It is also unfavorable to subject the produced waste mixed acid to dehydration-concentration by distillation, because materials for the equipment are very limited and a large quantity of thermal energy is consumed.

According to the above-said prior art references 1 to 3, the yield of 1-nitroanthraquinone does not exceed 65% by weight.

Further, the crystals of 1-nitroanthraquinone obtained by the method described in said U.S. Pat. No. 3,766,222 and the prior art references 1 to 3 are too small to be separated by filtration on a large scale.

The present inventors have studied the nitration of anthraquinone using a mixed acid, and found the fact that most of the produced crude 1-nitroanthraquinone is suspended in the reaction medium and is separable from the liquid portion without adding water, and the fact that, when the nitration is carried out in a mixed acid comprising 70 to 76% sulfuric acid and such an amount of nitric acid that the content of pure nitric acid ranges from 33 to 55% by weight based on the total weight of the acid, it is possible to obtain 1-nitroanthraquinone in the form of large crystal having good filterability in a high yield, and to reuse the separated mixed acid for the nitration of anthraquinone with little or no treatment.

The present invention provides a method for producing 1-nitroanthraquinone by nitration of anthraquinone, which comprises reacting anthraquinone at a temperature of 30° to 80° C. with a mixed acid comprising sulfuric acid and nitric acid, the concentration of sulfuric acid being 70 to 76% by weight and the amount of nitric acid being 33 to 55% by weight based on the total weight of sulfuric acid and nitric acid, then separating the reaction mixture into a crystal portion of 1-nitroanthraquinone and a liquid portion of the mixed acid.

The accompanying drawing diagrammatically shows the relationship among the quantitites of sulfuric acid, nitric acid and water. The shaded portions (A) and (B) indicate the composition ranges of the mixed acid of the present invention and U.S. Pat. No. 3,766,222 respectively.

As is apparent from the FIGURE, the composition (B) consists of 70 to 90% sulfuric acid and 90 to 100% nitric acid, the amount of nitric acid being 16.7 to 30% by weight based on the total weight of the acids, and therefore the composition (A) of the present invention is different from the composition (B) in that the composition (A) is lower in the concentration of sulfuric acid, and is larger in the amount of nitric acid, than those of the composition (B).

In carrying out the method of the present invention the initial amount of the mixed acid of this invention is 7 to 15 parts by weight, preferably 8 to 12 parts by weight, per part by weight of anthraquinone. The reaction temperature is 30° to 80° C., preferably 40 to 60° C. The nitration is carried out for 3 to 32 hours under the above-described conditions, whereby there is obtained crude 1-nitroanthraquinone having a purity of 76% by weight (mean value), a crystal size of about 30 to 200μ and very good filterability. In this case, the rate of filtration is improved to 5 to 20 times as fast as that of the well-known methods. All or a part of the recovered mixed acid can be recycled to the next nitration process without change in the yield and crystallinity of the crude 1-nitroanthraquinone produced.

The method of the present invention is illustrated in more detail as follows.

Anthraquinone is suspended in sulfuric acid of a desired concentration (the concentration depends on the concentration and amount of nitric acid to be added and is finally adjusted to 70 to 76% by weight), the mixture is heated to the reaction temperature (30° to 80° C.) and then nitric acid having a concentration of at least 85% is added dropwise thereto at the same temperature to adjust the composition of the resulting mixed acid to the above-defined one. Alternatively, anthraquinone is suspended in a mixed acid which is low in total acid concentration and a mixed acid which is high in total acid concentration is gradually added thereto, thus adjusting the composition of the resulting mixed acid to the above-defined one. This process is suitable for cyclic use of the recovered mixed acid. Further, there is a process wherein anthraquinone is suspended in a mixed acid which is low in total acid concentration and then concentrated sulfuric acid is added thereto, thus controlling the rate of reaction. Still further, there may be employed a process wherein anthraquinone is mixed with the total amount of a mixed acid having the above-defined composition at a low temperature and then the mixture is heated to the reaction temperature. In any process, it is important that the nitration is carried out using the composition within the range (defined above).

The total acid concentration is lowered with the progress of the nitration so that the rate of nitration is also lowered. In order to shorten the reaction time, therefore, it is favorable to carry out the nitration while gradually increasing the reaction temperature or substantially maintaining the initial DVS (weight ratio of sulfuric acid to water in the reaction system) during the reaction.

The reaction is continued to the extent that a desired amount of 1-nitroanthraquinone has just been produced, for example, the conversion of anthraquinone fed reaches about 50% or more. The end point can be determined by analyzing a part of the reaction mixture with the lapse of reaction time. When the reaction is repeated under the same conditions, the reaction time once determined is used thereafter as a standard.

The reaction is terminated by cooling the reaction mixture to 30° C. or below and/or adding a small amount of water or a dilute sulfuric acid to the reaction mixture. The former (cooling the reaction mixture) is preferred because the mixed acid recovered can be reused for the next nitration as it is, and because the addition of a diluent tends to make the crystals so small that filterability becomes poor.

The waste mixed acid separated by filtration or centrifugal sedimentation contains organic substances in small amounts, but all or part of it may be used for the next nitration process. The acid attached to the crude 1-nitroanthraquinone is difficultly separable so that the recovery of the mixed acid is generally within the range of 70 to 96%. The recovery of the mixed acid is a function of the solid content of the filtered crude 1-nitroanthraquinone. In order to increase the recovery, it is necessary to increase the degree of squeeze on filtration.

Although it is in general undesirable in terms of safety to carry out the filtration or centrifugation of a liquid slurry of a high acid concentration containing a large amount of nitric acid, and moreover separation equipments must be fairly limited, the liquid slurry resulting from the method of the present invention can be subjected to the filtration or centrifugation without any limitation, because the crude 1-nitroanthraquinone obtained by the method of this invention is easily separable without any particular aftertreatment (for example, a treatment of promoting the growth of crystals).

The crude 1-nitroanthraquinone obtained by separation from the mixed acid and neutralization or washing of the adhering acids, has the following composition on the average. All percentages are by weight.

1-Nitroanthraquinone: 76.5%
1,5-Dinitroanthraquinone: 5.0%
1,8-Dinitroanthraquinone: 3.6%
1,6- And 1,7-dinitroanthraquinones: 10.1%
2-Nitroanthraquinone: 2.3%
Anthraquinone: 0.9%

If expressed by mole percent, the above content of 1-nitroanthraquinone is about 80 mole %.

The crude 1-nitroanthraquinone mixture obtained by the method of this invention can be subjected to a conventional reduction as it is, and the resulting aminoanthraquinone mixture can be purified by vacuum distillation, or the crude 1-nitroanthraquinone mixture can be purified by vacuum distillation or with a sulfite, and thereafter subjected to a conventional reduction, whereby 1-aminoanthraquinone is obtained in a high purity and high yield.

The quality of 1-aminoanthraquinone thus obtained and the qualities of dyes and pigments derived therefrom are comparable to those of 1-aminoanthraquinone obtained by sulfonation of anthraquinone with mercury as catalyst followed by amination and those of dyes and pigments derived therefrom.

The present invention will be illustrated specifically with reference to the following examples and reference examples. But the present invention is not limited to these examples.

EXAMPLE 1

In 30 kg of 73.8% sulfuric acid in a nitration reactor was suspended 5 kg of anthraquinone, and 15.3 kg of 99% nitric acid was added over 1 hour at 50° C. After stirring for 14 hours at this temperature, the reaction mixture was cooled to 30° C. to stop the reaction. The crude 1-nitroanthraquinone obtained had a purity of 77.4% (see Table 1). Thereafter, 4.5 kg of the reaction mixture was pressure-filtered at 30° C. under 1 atm., using polypropylene fiber filter cloth (filter area 113 cm$^2$). It took 5 minutes for the filtration. The crude 1-nitroanthraquinone thus obtained was mainly composed of columnar crystals of 30 to 100$\mu$ in length and 5 to 10$\mu$ in width.

In this example, the nitration did not occur until almost all of nitric acid had been added and then the composition of the resulting mixed acid had reached the range (A) in the accompanying drawing.

EXAMPLE 2

Into 37.5 kg of a mixed acid (sulfuric acid 52.0%, nitric acid 28.1%, water 19.9%) was charged 5 kg of anthraquinone at room temperature. After stirring thoroughly, the mixture was heated to 50° C. Thereafter, 7.9 kg of a mixed acid (sulfuric acid 33.7%, nitric acid 58.2%, water 8.1%) was added thereto over 6 hours at this temperature. After stirring for 11 hours at this temperature, the reaction mixture was cooled to 30° C. to stop the reaction. Thus, the nitration product having the composition as shown in Table 1 was obtained. The filtration test was carried out in the same manner as in Example 1 and it took a filtration time of 6 minutes. The size of crystals was also the same as in Example 1.

EXAMPLE 3

In 30 kg of 76.1% sulfuric acid was suspended 5 kg of anthraquinone, and 18.4 kg of 98.5% nitric acid was added thereto at room temperature. After the addition was finished, the mixture was stirred for 8 hours while maintaining the temperature at 40° C. After completion of the reaction was confirmed by gas chromatography, the reaction mixture was cooled to 25° C. to stop the reaction. Thus, the nitration product of anthraquinone having the composition as shown in Table 1 was obtained. The filtration was carried out at 25° C. using the same filter as in Example 1 and it took a filtration time of 4 minutes.

EXAMPLE 4

In 30 kg of 72.5% sulfuric acid in a nitration reactor was suspended 5 kg of anthraquinone, and 21.2 kg of 99.7% nitric acid was added over 1 hour at 50° C. After stirring for 4 hours at this temperature, the reaction mixture was cooled to 30° C. to stop the reaction. Thus, the nitration product having the composition as shown in Table 1 was obtained. The filtration test was carried out in the same manner as in Example 1 and it took a filtration time of 6 minutes.

EXAMPLE 5

In 32.5 kg of 73.7% sulfuric acid in a nitration reactor was suspended 5 kg of anthraquinone, and 15.4 kg of 98.5% nitric acid was added over 1 hour at 50° C. After stirring for 16 hours at this temperature, the reaction mixture was cooled to 30° C. to stop the reaction. Thus, the nitration product having the composition as shown in Table 1 was obtained. The filtration test was carried out in the same manner as in Example 1 and it took a filtration time of 5 minutes.

EXAMPLE 6

Into 38.5 kg of the mixed acid which was the filtrate (sulfuric acid 51.3%, nitric acid 27.1%, water 20.6%, organic materials 1.0%) obtained by the reaction in Example 2 was charged 5 kg of anthraquinone at room temperature. After stirring thoroughly, the mixture was heated to 50° C. Thereafter, 7.3 kg of a fresh mixed acid (sulfuric acid 33.1%, nitric acid 64.7%, water 2.2%) was added thereto over 6 hours at this temperature. After stirring for 13 hours at this temperature, the reaction mixture was cooled to 30° C. to stop the reaction. Thus, the nitration product having the composition as shown in Table 1 was obtained. The filtration test was carried out in the same manner as in Example 2 and it took a filtration time of 6 minutes.

EXAMPLE 7

Into 38.7 kg of the mixed acid which was the filtrate (sulfuric acid 50.1%, nitric acid 28.1%, water 20.0%, organic materials 1.8%) obtained by the reaction in Example 6 was charged 5 kg of anthraquinone at room temperature. After stirring thoroughly, the mixture was heated to 50° C. Thereafter, 7.4 kg of a fresh mixed acid (sulfuric acid 37.5%, nitric acid 57.6%, water 4.9%) was added thereto over 6 hours at this temperature. After stirring for 15 hours at this temperature, the reaction mixture was cooled to 30° C. to stop the reaction. Thus, the nitration product having the composition as shown in Table 1 was obtained. The filtration was carried out at 30° C. in the same manner as in Example 6 and it took a filtration time of 6 minutes. The size of crystals was also the same as in Example 6.

EXAMPLE 8

Shortening of reaction time

The procedure was carried out in the same manner as in Example 7, except that after addition of the fresh mixed acid was completed, 1.4 kg of 100% sulfuric acid was gradually added thereto over 2 hours and then the mixture was kept at 50° C. for further 1 hour. After completion of the reaction was confirmed, the reaction mixture was cooled to 30° C. to stop the reaction. As a result, the filtration time, the size of crystals and the composition of nitration product were almost the same as in Example 7. Further, in the case where, after the additional mixed acid was added, the reaction temperature was elevated from 50° C. to 60° C., the reaction time was shortened but the yield of 1-nitroanthraquinone was decreased by 2 to 3%.

REFERENCE EXAMPLE 1

Method of the examples of U.S. Pat. No. 3,766,222.

In 38.5 kg of 78% sulfuric acid was suspended 5 kg of anthraquinone, and 12.3 kg of 98% nitric acid was then added dropwise at room temperature over 1 hour. In this case, the temperature of the nitration mixture was adjusted so as to reach 40° C. at the end of the addition of the nitric acid. The nitration mixture was stirred for 12 hours at this temperature. The nitroanthraquinone mixture at that time had the composition as shown in Table 1. Thereafter, 4.5 kg of the reaction mixture was cooled to 30° C. and pressure-filtered under 1 atm. using polypropylene fiber filter cloth (filter area 113 cm$^2$). It took 54 minutes for the filtration.

The crude 1-nitroanthraquinone obtained by the filtration had columnar crystals of 3 to 10$\mu$ in length and 1 to 2$\mu$ in width.

REFERENCE EXAMPLE 2

Follow-up experiment on U.S. Pat. No. 2,302,729.

In 33.5 kg of 87% sulfuric acid was suspended 5 kg of anthraquinone and 5.34 kg of a mixed acid (sulfuric acid 66.4%, nitric acid 32.3%, water 1.3%) was added over 1 hour at 30° to 35° C. Thereafter, the nitration mixture was heated to 65° to 70° C. and kept at this temperature for 3 hours. Thus, the nitration product having the composition as shown in Table 1 was obtained. Thereafter, 4.5 kg of the reaction mixture was cooled to 30° C. and pressure-filtered under 1 atm. using the same filter as in Reference Example 1. It took 900 minutes for the filtration.

TABLE 1

| | Composition of nitration product (weight %) | | | | | |
|---|---|---|---|---|---|---|
| | I | II | III | IV | V | VI |
| Example 1 | 77.4 | 0.8 | 2.2 | 4.8 | 3.2 | 10.0 |
| Example 2 | 75.4 | 0.7 | 0.2 | 5.3 | 5.0 | 12.2 |
| Example 3 | 75.3 | 0.7 | 3.2 | 6.2 | 4.5 | 8.1 |
| Example 4 | 77.3 | 1.5 | 5.9 | 4.9 | 3.7 | 4.6 |
| Example 5 | 76.2 | 1.4 | 3.0 | 4.3 | 3.1 | 9.4 |
| Example 6 | 77.8 | 0.7 | 0.5 | 4.8 | 4.5 | 10.6 |
| Example 7 | 75.4 | 1.1 | 1.5 | 4.0 | 3.6 | 10.0 |
| Reference Example 1 | 75.5 | 0.9 | 0.3 | 5.2 | 3.6 | 12.6 |

TABLE 1-continued

| | Composition of nitration product (weight %) | | | | | |
|---|---|---|---|---|---|---|
| | I | II | III | IV | V | VI |
| Example 2 | 61.0 | 12.0 | 3.8 | 5.1 | 5.5 | 9.0 |

I 1-Nitroanthraquinone
II Anthraquinone
III 2-Nitroanthraquinone
IV 1,5-Dinitroanthraquinone
V 1,8-Dinitroanthraquinone
VI 1,6- And 1,7-dinitroanthraquinones

What is claimed is:

1. A method for producing 1-nitroanthraquinone by nitration of anthraquinone, which comprises reacting anthraquinone at a temperature of 30° to 80° C. with a mixed acid comprising sulfuric acid and nitric acid, the concentration of sulfuric acid being 70 to 76% by weight and the amount of nitric acid being 33 to 55% by weight based on the total weight of sulfuric acid and nitric acid, and then separating the reaction mixture into a crystal portion of 1-nitroanthraquinone and a liquid portion of the mixed acid.

2. A method according to claim 1, wherein all or a part of the liquid portion is reused for the reaction.

3. A method according to claim 1, wherein the mixed acid is used in an amount of 7 to 15 parts by weight per part by weight of anthraquinone.

4. A method according to claim 1, wherein the reaction is carried out while gradually increasing the reaction temperature or substantially maintaining the initial DVS value during the reaction.

5. A method according to claim 1, wherein the reaction is terminated by cooling the reaction mixture to a temperature of 30° C. or below.

6. A method according to claim 1, wherein the separation is conducted by filtration.

* * * * *